United States Patent
Kim

(10) Patent No.: US 9,950,022 B2
(45) Date of Patent: Apr. 24, 2018

(54) SEXUAL FUNCTION IMPROVING COMPOSITION CONTAINING AS ACTIVE INGREDIENT EXOPOLYSACCHARIDE PRODUCED BY MEANS OF CERIPORIA LACERATA

(71) Applicant: FUGENBIO CO., LTD., Seoul (KR)

(72) Inventor: Yoon Soo Kim, Seongnam-si (KR)

(73) Assignee: FUGENBIO CO., LTD., Seoul (KR)

( * ) Notice: Subject to any disclaimer, the term of this patent is extended or adjusted under 35 U.S.C. 154(b) by 0 days.

(21) Appl. No.: 15/523,526

(22) PCT Filed: Nov. 3, 2015

(86) PCT No.: PCT/KR2015/011722
§ 371 (c)(1),
(2) Date: May 1, 2017

(87) PCT Pub. No.: WO2016/072713
PCT Pub. Date: May 12, 2016

(65) Prior Publication Data
US 2017/0312325 A1    Nov. 2, 2017

(30) Foreign Application Priority Data

Nov. 3, 2014   (KR) ......................... 10-2014-0151578

(51) Int. Cl.
| | | |
|---|---|---|
| *A61K 36/07* | (2006.01) | |
| *A23G 3/36* | (2006.01) | |
| *A23L 2/52* | (2006.01) | |
| *A23L 33/00* | (2016.01) | |
| *A23L 33/10* | (2016.01) | |
| *A23G 1/42* | (2006.01) | |
| *A61K 31/715* | (2006.01) | |
| *A23G 4/12* | (2006.01) | |

(52) U.S. Cl.
CPC ................ *A61K 36/07* (2013.01); *A23G 1/42* (2013.01); *A23G 3/364* (2013.01); *A23G 4/12* (2013.01); *A23L 2/52* (2013.01); *A23L 33/10* (2016.08); *A23L 33/30* (2016.08); *A23L 33/40* (2016.08); *A61K 31/715* (2013.01); *A23V 2002/00* (2013.01)

(58) Field of Classification Search
CPC ....... A61K 36/07; A61K 31/715; A23L 33/30; A23L 33/40; A23L 2/52; A23L 33/10; A23G 1/42; A23G 3/364; A23G 4/12; A23V 2002/00
USPC ......................................................... 514/479
See application file for complete search history.

(56) References Cited

FOREIGN PATENT DOCUMENTS

| KR | 10-0942794 B1 | 2/2010 |
|---|---|---|
| KR | 10-1031605 B1 | 4/2011 |
| KR | 10-2011-0090217 A | 8/2011 |
| WO | 2014/112665 A1 | 7/2014 |

OTHER PUBLICATIONS

Ji-Eun Kim, et al., "Hyperglycemic Effect of Submerged Culture Extract of *Ceriporia lacerata* in Streptozotocin-induced Diabetic Rats", Food Sci., Biotechnol., Dec. 31, 2012, pp. 1685-1693, vol. 21, No. 6.
International Searching Authority, International Search Report for PCT/KR2015/011722 dated Feb. 12, 2016 [PCT/ISA/210].
International Searching Authority, Written Opinion for PCT/KR2015/011722 dated Feb. 12, 2016 [PCT/ISA/237].

*Primary Examiner* — Kristin A Vajda
(74) *Attorney, Agent, or Firm* — Sughrue Mion, PLLC

(57) ABSTRACT

The present invention relates to a sexual function improving composition containing as an active ingredient: exopolysaccharide produced by means of *Ceriporia lacerata*; a *Ceriporia lacerata* mycelium culture medium comprising the exopolysaccharide; dry powder of the mycelium culture medium; or an extract of the mycelium culture medium. The composition can be used as a sexual function improving drug for preventing or treating erectile dysfunction or diabetic erectile dysfunction or as a functional health food having sexual function improving effect.

12 Claims, 1 Drawing Sheet

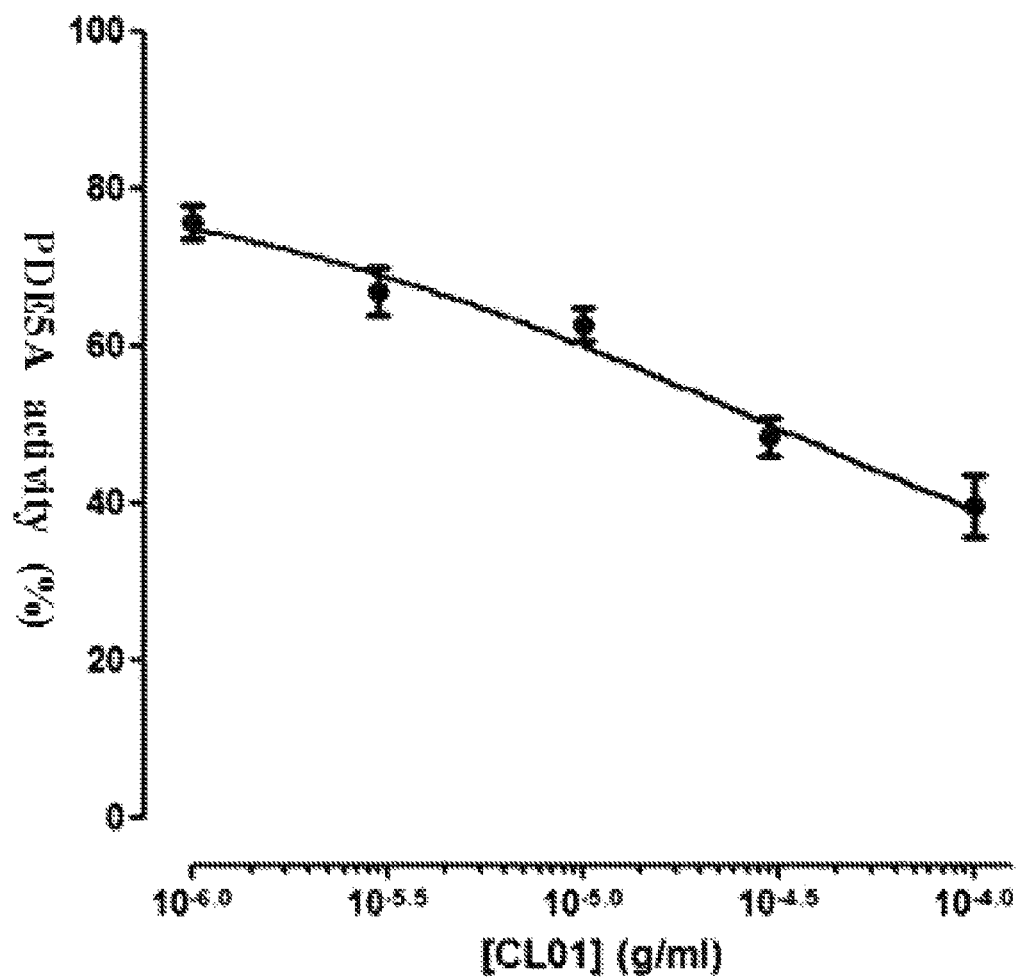

SEXUAL FUNCTION IMPROVING COMPOSITION CONTAINING AS ACTIVE INGREDIENT EXOPOLYSACCHARIDE PRODUCED BY MEANS OF CERIPORIA LACERATA

CROSS REFERENCE TO RELATED APPLICATIONS

This application is a National Stage of International Application No. PCT/KR2015/011722 filed Nov. 3, 2015, claiming priority based on Korean Patent Application No. 10-2014-0151578 filed Nov. 3, 2014, the contents of all of which are incorporated herein by reference in their entirety.

TECHNICAL FIELD

The present invention relates to a composition for improving sexual function comprising, an extracellular polysaccharide produced by *Ceriporia lacerata*, a mycelial culture medium of *Ceriporia lacerata* containing the same, or dried powders or an extract of the mycelial culture medium, as an effective ingredient.

BACKGROUND ART

Male sexual function consists of sexual desire, penile erection, ejaculation and extreme feeling. The penile erection is induced by gradual increase of the pressure within the penis. The internal pressure of the penis increases by the stimulation of the erectile nerve which leads to the expansion of sinusoids due to relaxation of smooth muscle of corpus cavernosum and increased blood flow due to the dilatation of arterioles. The internal pressure of the penis increases more by venous outflow blockage due to the compression of subtunical vein between a relatively hard tunica albuginea and sinusoids by expanded sinusoids.

According to statistics, about 20% to 60% of adult males suffer from sexual dysfunction, and the incidence thereof increases with age. Although these sexual dysfunctions were considered to occur mostly by psychogenic causes about 10 years ago, the development of modern medicine, reveals that the onset of sexual dysfunctions in about 50% or more of the sexual dysfunction patients is caused by other causes such as vascular, neurological and endocrine disorders, diabetics, hypertension, drug intake, etc.

Recently it is known that sildenafil (Viagra®), which has been developed as an oral agent for erectile dysfunction and used worldwide, shows a therapeutic effect on erectile dysfunction by increasing the concentration of cGMP by the inhibition of PDE-5 (phosphodiesterase-5) specifically distributed in the corpus cavernosum, which increases the blood flow in the corpus cavernosum, and thus inducing erection. In addition, PDE-5 inhibitors generally known as erectile dysfunction therapeutic agents include selective inhibitors of cyclic guanosine 3',5'-monophosphate-specific phosphodiesterase type 5 (cGMP-specific PDE-5) such as Udenafil ($C_{25}H_{36}N_6O_4S$), Sildenafil ($C_{22}H_{30}N_6O_4S$), Vardenafil ($C_{23}H_{32}N_6O_4S$), Tadalafil ($C_{22}H_{19}N_3O_4$) and the like, which are disclosed in Korean Patent No. 0353014 (Udenafil), Korean Patent No. 0262926 (Sildenafil), Korean Patent No. 0430355 (Vardenafil), and Korean Patent No. 0357411 (Tadalafil). However, pre-existing drugs are reported to show various adverse events such as headache, facial flushing, dyspepsia, cardiac arrest, etc., and thus there is a need for a new drug that can replace or supplement the pre-existing drugs.

Therefore, it is required to develop a male sexual function-improving agent which does not show adverse events of pre-existing treatment methods and comprises a main ingredient which is not a chemically synthesized product but a natural substance. The clinical efficacy of natural products have been proven since long before and they generally show fewer adverse events than chemical substances, rendering them suitable candidates for the development of a composition for improving sexual function.

*Ceriporia lacerata* is a kind of white-rotting fungus and known to conduct co-metabolism, i.e., lignin decomposition, in order to use carbon sources such as cellulose, hemicellulose, other polysaccharides, and glycerol, etc., in the ecosystem. However, since *Ceriporia lacerata* was first reported to academic world in 2002, the research on the industrialization of *Ceriporia lacerata* has not been done sufficiently.

Accordingly, the present inventors have found that an extracellular polysaccharide produced by *Ceriporia lacerata*; a mycelial culture medium of *Ceriporia lacerata* containing the same, or dried powders or an extract thereof shows a sexual function-improving effect, and have completed the present invention which is related to a composition for improving sexual function comprising the extracellular polysaccharide, the mycelial culture medium, dried powders, or the extract, as an effective ingredient.

DISCLOSURE OF INVENTION

Technical Problem

It is an object of the present invention to provide a composition for improving sexual function comprising a pharmacologically active ingredient produced by *Ceriporia lacerata*.

It is another object of the present invention to provide a health functional food for improving sexual function, comprising a pharmacologically active ingredient produced by *Ceriporia lacerata*.

Solution to Problem

In accordance with one object of the present invention, there is provided a composition for improving sexual function comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient.

In accordance with another object of the present invention, there is provided a health functional food for improving sexual function, comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient.

In accordance with another object of the present invention, there is provided a method for improving sexual function comprising administering to a subject in need of improving sexual function an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium.

In accordance with another object of the present invention, there is provided a use of an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium for preparing a drug for improving sexual function.

Advantageous Effects of Invention

A composition comprising an extracellular polysaccharide produced by *Ceriporia lacerata*; a mycelial culture medium of *Ceriporia lacerata* containing the same, or dried powders or an extract thereof, as an effective ingredient, shows inhibitory effect on PDE-5 activity, and thus can be usefully employed for improving sexual function.

BRIEF DESCRIPTION OF DRAWINGS

FIG. 1 is a graph showing the inhibitory effect of an extracellular polysaccharide produced by *Ceriporia lacerata* on PDE-5 activity.

BEST MODE FOR CARRYING OUT THE INVENTION

Hereinafter, the present invention is explained in detail.

In the present invention, there is provided a composition for improving sexual function, which contains an extracellular polysaccharide produced by *Ceriporia lacerata*; a mycelial culture medium of *Ceriporia lacerata* containing the extracellular polysaccharide; dried powders of the mycelial culture medium, or an extract of the mycelial culture medium, as an effective ingredient.

In a composition according to the present invention, the extracellular polysaccharide may comprise about 40 to 60 wt % of sugar and about 30 to 40 wt % of protein, about 40 to 50 wt % of sugar and about 32 to 38 wt % of protein, or about 43 to 47 wt % of sugar and about 33 to 36 wt % of protein, preferably about 45 wt % of sugar and about 34 wt % of protein.

The sugar may contain mannose, galactose and glucose.

The extracellular polysaccharide may have a molecular weight of about 100 to 150 kDa, about 110 to 140 kDa or about 115 to 125 kDa, preferably about 120 kDa.

According to one preferred embodiment of the present invention, the extracellular polysaccharide may be prepared by a preparation method comprising the steps of: (a) culturing mycelia of *Ceriporia lacerata* in a liquid to prepare a mycelial culture medium of *Ceriporia lacerata*, (b) drying the mycelial culture medium of *Ceriporia lacerata* to form powders, and (c) extracting the powders of the mycelial culture medium of *Ceriporia lacerata* with a solvent, and filtering and concentrating the resultant extract under reduced pressure.

The medium for culturing in a liquid in the step (a) may contain sugar, glucose, starch, sorghum powder, barley powder, soybean flour, magnesium sulfate ($MgSO_4$), monopotassium phosphate ($KH_2PO_4$), dipotassium phosphate ($K_2HPO_4$) and water, and the hydrogen ion concentration (pH) of the medium may be 4.5 to 6.0.

According to one preferred embodiment of the present invention, the medium may contain 0.2 to 3 wt % of sugar, 0.2 to 3 wt % of glucose, 0.2 to 4 wt % of starch, 0.1 to 0.5 wt % of sorghum powder, 0.1 to 0.5 wt % of barley powder, 0.2 to 3 wt % of soybean flour, 0.05 to 0.1 wt % of magnesium sulfate (MgSO4), 0.05 to 0.25 wt % of monopotassium phosphate ($KH_2PO_4$), 0.05 to 0.25 wt % of dipotassium phosphate ($K_2HPO_4$) and residual quantity of water.

The culture in a liquid of the step (a) may be conducted under a blue LED light source, and may be conducted with a carbon dioxide concentration maintained at 1,000 to 2,000 ppm.

For example, the culture in a liquid may be conducted for 8 to 13 days at 20 to 25° C., under a blue LED light source, with the pH maintained at 4.5 to 6.0, an illuminance maintained at 0.5 LUX, an air injected at 0.5 to 1.5 kgf/cm², and carbon dioxide concentration maintained at 1,000 to 2,000 ppm, and preferably, the culture is conducted for 10 days under the condition of 22° C., pH 5.0, 1.0 kgf/cm², and 1,500 ppm, to obtain a high content of an extracellular polysaccharide.

The parent strain for use in step (a) may be a strain obtained by culturing a dominant strain stored in PDA (Potato dextrose agar) medium at 4° C. in PDB (Potato dextrose broth) medium in Erlenmeyer flask using a shaking incubator at a constant temperature of 25° C. for 7 to 9 days. Herein, the amount of the mycelium to be inoculated is preferably about 0.5% (w/v) based on the solution to be cultured. Since a high amount of the mycelia (%/100 mL) does not necessarily result in a high content of the extracellular polysaccharide, the medium composition may be preferably selected such that it provides a condition for maximizing the content of extracellular polysaccharide, rather than the best condition for the growth of mycelia.

The culture medium may be separated and purified into mycelia and an aqueous solution. For the separation and purification, the mycelia may be removed from the culture medium using a centrifuge and the remaining solution may be repeatedly purifed using a Multi-Sheet Filter Press and a vibrating membrane separator (PALLSEP), followed by irradiation with UV rays for 1 minute. Also, the solution needs to be sealed and stored after removing oxygen, since the presence of mycelia in the solution results in the change in the content of the effective ingredient due to the growth of the mycelia induced by oxygen.

In step (b), the mycelial culture medium prepared in step (a) may be vacuum dried or freeze dried to form powders. In order to prevent the loss of an effective substance, the drying is preferably carried out at a temperature of 40° C. or lower, preferably 30° C. or lower, for 48 to 96 hours. In addition, for the drying in step (b), a vacuum freeze dryer is preferably used rather than a vacuum dryer in which a relatively high evaporation temperature is set, in terms of minimizing the change in the content of the effective substance.

In step (c), the dried powders of a mycelial culture medium obtained in step (b) are extracted with a solvent, an extracellular polysaccharide, an effective ingredient according to the present invention, is isolated and prepared.

Specifically, 100 mL of distilled water may be added to 5 g of dried powders, and the resultant suspension may be centrifuged (8,000 rpm, 20 min), and then, a 2 to 3-fold amount of extraction solvent may be added to the supernatant, and the resulting solution may be placed in a refrigerator (4° C.) and allowed to stand for 12 hours. The supernatant in the solution which had been allowed to stand may be obtained and centrifuged again (8,000 rpm, 20 min), and the precipitate may be recovered, thereby preparing a crude extracellular polysaccharide. The crude extracellular polysaccharide is preferably vacuum freeze dried at a temperature of 30° C. or lower.

The extraction solvent may be a solvent selected from the group consisting of water, ethanol, methanol, acetone, butanol and ethyl acetate, or a mixture thereof, and preferably, it may be water or 50% (w/w) to 80% (w/w) of aqueous solution of ethanol.

A composition for improving sexual function according to the present invention comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient, may further contain a carrier, an excipient and a diluent which are commonly used.

The extracellular polysaccharide may be comprised in an amount of 0.1 to 80 wt %, preferably 0.1 to 50 wt %, based on the total weight of the composition, and a mycelial culture medium of *Ceriporia lacerata*, or dried powders or an extract thereof may be adequately comprised in an amount which corresponds to the above amount of the extracellular polysaccharide. However, the most preferred effective content of an extracellular polysaccharide, a mycelial culture medium containing the extracellular polysaccharide, or dried powders or an extract thereof may be adequately adjusted according to the method of use and purpose of the composition.

A composition according to the present invention can be formulated and used in accordance with a conventional method. Suitable formulations may include, but are not limited to, tablets, pills, powders, granules, sugar-coated tablets, hard or soft capsules, solutions, suspensions or emulsions, injections, suppositories, and the like.

A composition according to the present invention can be prepared into a suitable formulation using a pharmaceutically inert organic or inorganic carrier. That is, if the formulation is a tablet, a coated tablet, a sugar-coated tablet or a hard capsule, lactose, sucrose, starch or a derivative thereof, talc, calcium carbonate, gelatin, or stearic acid or a salt thereof may be used. Also, if the formulation is a soft capsule, vegetable oil, wax, fat, or semi-solid or liquid polyol may be used. Furthermore, if the formulation is in the form of a solution or syrup, water, polyol, glycerol, vegetable oil, and the like may be used.

A composition according to the present invention may further comprise a preservative, a stabilizer, a wetting agent, an emulsifier, a solubilizer, a sweetener, a coloring agent, an osmotic pressure regulator, an antioxidant, and the like in addition to the above carrier.

A method of administering a composition according to the present invention can be easily selected in accordance with the formulation, which may be oral or parenteral administration. The dosage may vary depending on the patient's age, sex, weight, disease severity, and/or route of administration, but is generally 5 to 500 mg/kg, preferably 100 to 250 mg/kg based on the extracellular polysaccharide, an effective ingredient, which may be administered in one to three divided doses a day. However, such dosage does not limit the scope of the present invention in any way.

A composition according to the present invention not only provides an excellent sexual function-improving effect but also shows little toxicity and adverse events, and thus can safely be used for the purpose of sexual function improvement by long-term administration. Therefore, a composition of the present invention can be used for preventing and treating a disease requiring sexual function improvement such as, for example, erectile dysfunction, diabetic erectile dysfunction, etc.

Furthermore, the present invention provides a health functional food for improving sexual function, comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient A health functional food according to the present invention may be in the form of powders, granules, a tablet, a capsule or a drink, and may be a candy, a chocolate, a drink, a gum, a tea, a vitamin complex, a health supplementary food, and the like.

Herein, an extracellular polysaccharide, a mycelial culture medium containing the extracellular polysaccharide, or dried powders or an extract thereof according to the present invention may be generally comprised in a food in an amount of 0.01 to 50 wt %, preferably 0.1 to 20 wt % based on the total weight of the food, and may be generally comprised in a ratio of 0.02 to 10 g, preferably 0.3 to 1 g based on 100 mL of a health drink composition in the case of a health drink composition.

The food may further comprise a sitologically acceptable food supplementary additive in addition to an extracellular polysaccharide produced by *Ceriporia lacerate*; a mycelial culture medium of *Ceriporia lacerata* containing the extracellular polysaccharide; dried powders of the mycelial culture medium; or an extract of the mycelial culture medium.

The present invention provides a method for improving sexual function comprising administering to a subject in need of improving sexual function an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium.

The subject in need of improving sexual function may be a mammal, specifically human.

In addition, the present invention provides a use of an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium for preparing a drug for improving sexual function.

The extracellular polysaccharide produced by *Ceriporia lacerata*; the mycelial culture medium of *Ceriporia lacerata* containing the extracellular polysaccharide; dried powders of the mycelial culture medium; or an extract of the mycelial culture medium are as described above.

In addition, the method for improving sexual function can be used for preventing or treating a disease requiring sexual function improvement such as, for example, erectile dysfunction or diabetic erectile dysfunction.

MODE FOR THE INVENTION

Hereinafter, the present invention will be described in more detail with the following Examples. The following Examples are provided to illustrate the present invention, but the scope of the present invention is not limited thereto.

EXAMPLES

1. Preparation of Culture Medium of *Ceriporia lacerata*, Dried Powders Thereof, Extract, and Extracellular Polysaccharide (Exopolysaccharide, Hereinafter Referred to as "EPS")

1.1 Preparation of Culture Medium of *Ceriporia lacerata*

*Ceriporia lacerata* isolated from *Quercus serrata* collected at Sangju city, Gyeongbuk province were subcultured to obtain a parent strain which was subsequently freeze-stored at −80° C., and the freeze-stored strain was cultured with 2-3 passages in PDA (Potato dextrose agar) medium (87 plastic bulbs, Difco, Becton Dickinson and Company), and the strain (hereinafter referred to as "PDA culture strain") was stored in a refrigerator at 4° C. until use. Then, 600 mL of the PDB (Potato dextrose broth) medium (Difco, Becton Dickinson and Company) was placed in an Erlenmeyer flask, and a PDA culture strain was added thereto and shake-cultured at 25° C. for 8 days to obtain a PDB culture strain.

Thereafter, a liquid culture medium containing 1.5 wt % of sugar, 0.5 wt % of glucose, 0.5 wt % of potato starch, 0.25 wt % of sorghum powder, 0.25 wt % of barley powder, 0.75 wt % of soybean flour, 0.05 wt % of magnesium sulfate ($MgSO_4$), 0.05 wt % of monopotassium phosphate ($KH_2PO_4$), 0.05 wt % of dipotassium phosphate ($K_2HPO_4$) and residual quantity of water was sterilized for 20 minutes in a 800 L fermenter with the air of 121° C. injected at 1.5 $kgf/cm^2$, and then, the medium was cooled to 23° C. and inoculated with 600 mL of the PDB culture strain as a starter. *Ceriporia lacerata* mycelia were liquid-cultured in the medium for 10 days at a constant temperature of 23° C., under a blue LED light source, with the air injected at 0.5 to 1.5 $kgf/cm^2$, an illuminance maintained at 0.5 LUX, and a carbon dioxide concentration of 2,000 ppm, to prepare the mycelial culture medium of *Ceriporia lacerata*.

1.2 Preparation of Dried Powders of Culture Medium of *Ceriporia lacerata*

The mycelial culture medium of *Ceriporia lacerata* prepared in the Preparation Example 1.1 was vacuum-freeze-dried by a vacuum freeze dryer at 25° C. for 72 hours to form powders, thereby preparing dried powders of a mycelial culture medium of *Ceriporia lacerata*.

1.3 Preparation of Extract of Culture Medium of *Ceriporia lacerata*

5 g of dried powders of the mycelial culture medium of *Ceriporia lacerata* prepared in Preparation Example 1.2 was added to 100 mL of distilled water and sufficiently suspended, and then the resulting solution was centrifuged at 8,000 rpm for 20 minutes. The supernatant separated therefrom was mixed with a 2- to 3-fold amount of ethanol and allowed to stand at 4° C. for 12 hours. Thereafter, the resultant supernatant was taken and an extract of the mycelial culture medium of *Ceriporia lacerata* was prepared therefrom.

1.4 Preparation of EPS from Culture Medium of *Ceriporia lacerata*

The extract of the mycelial culture medium of *Ceriporia lacerata* prepared in Preparation Example 1.3 was further centrifuged at 8,000 rpm for 20 minutes, and then the precipitate was recovered to obtain crude EPS. The crude EPS was vacuum freeze dried in a vacuum freeze dryer at 25° C. for 72 hours to obtain an EPS produced by *Ceriporia lacerata*.

Example 1. Evaluation of EPS Properties 1.1. Molecular Weight Measurement of EPS Using Gel Permeation Chromatography (GPC)

The EPS prepared in Preparation Example 1 was dissolved in a solution of 0.1 M $Na_2SO_4$/0.05 M $NaN_3$ (adjusted to pH 4 with glacial acetic acid) to a concentration of 1% (w/v), and then the mixture was centrifuged at 4,000 rpm for 0.5 hour. The supernatant was isolated and filtered with a 0.45 μm syringe filter and analyzed by GPC.

Specifically, the refractive index of the detector was used for the GPC analysis, OHpak SB 805 HQ (Shodex, Japan) was used for the GPC column, and 0.1 M $Na_2SO_4$/0.05 M $NaN_3$ (adjusted to pH 4 with glacial acetic acid) was used for a mobile phase. The mobile phase was allowed to flow at a flow rate of 1.0 mL/min. Standard curves were generated using dextrans (American Polymer Corporation, USA) with different molecular weights (130 kDa, 400 kDa, 770 kDa or 1200 kDa), and the molecular weight of EPS was measured using refractive index (RI) measuring instrument Knauer K-2310 (Germany). The measurement conditions are summarized in Table 1 below.

TABLE 1

|  | Measurement of molecular weight |
| --- | --- |
| HPLC system | Knauer K-501 system |
| Column | OHpak SB 805 HQ (Shodex, Japan) |
| Mobile phase | 0.1M $Na_2SO_4$/0.05M $NaN_3$/pH 4 |
| Flow rate | 1.0 mL/min |
| Measuring instrument | RI (Knauer K-2310) |

As a result, the molecular weight of EPS of the present invention was about 120 kDa.

1.2. Measurement of Sugar and Protein Contents of EPS

The EPS prepared in Preparation Example 1 was subjected to secondary purification and treated with a protein-hydrolysis enzyme to measure sugar and protein contents.

Specifically, the primary-purified EPS (EPS prepared in Preparation Example 1) was dissolved in distilled water and centrifuged at 8,000 rpm for 20 minutes to separate the supernatant, and then a 2- to 3-fold amount of ethanol was added thereto. The mixture was placed and allowed to stand in a refrigerator at 4° C. for 12 hours. Thereafter, the resultant supernatant alone was centrifuged again at 8,000 rpm for 20 minutes, and the precipitate was recovered to obtain a secondary-purified EPS. The secondary-purified EPS was dissolved in distilled water and treated with Alcalase, a protein-hydrolysis enzyme, at a concentration of 0.5% (w/v) at 50° C. for 30 minutes.

Thereafter, the sugar content was measured by the phenol-sulfuric acid method. Specifically, 25 μL of 80% (v/v) phenol was added to 1 mL of each of the samples diluted at various concentrations, and then 2.5 mL of sulfuric acid was added thereto. The mixture was cooled to room temperature, and then the sugar content was calculated by measuring the absorbance at 465 nm.

Also, the protein content was measured by BCA method (Smith P K et al., *Analytical Biochemistry*, 150 (1): 76-85, 1985) and bovine serum albumin was used as a standard.

The sugar contents and protein contents measured as described above are shown in Table 2 below. The sugar content was 45 to 51 wt % and the protein content was 33 to 34 wt %.

TABLE 2

|  | Yield (%) | Total sugar content (%) | Total protein content (%) |
| --- | --- | --- | --- |
| EPS | 1.22 ± 0.03 | 45.32 ± 1.41 | 34.17 ± 0.73 |
| Secondary-purified EPS | 0.78 ± 0.01 | 50.49 ± 0.52 | 33.50 ± 2.79 |
| Enzyme-treated EPS* | 0.24 ± 0.06 | 51.39 ± 1.32 | 34.61 ± 1.51 |

*Enzyme treatment: Alkalase 0.5%, 50° C., 30 minutes.
Each value represents mean ± SE (n ≥ 3).

As a result of analyzing sugar content of EPS, it was found that EPS mainly contains mannose, galactose and glucose.

Example 2. Verification of Sexual
Function-Improving Effect of EPS

In order to investigate the sexual function-improving effect of EPS isolated from the mycelial culture medium of *Ceriporia lacerata*, the EPS prepared in Preparation Example 1 was placed in PDE-5A assay kit (available from BPS bioscience) at the concentrations of 1 μg/mL, 3 μg/mL, 10 μg/mL, 30 μg/mL and 100 μg/mL, and inhibitory effect of PDE-5 enzyme was measured with reference to the method described in a literature (Francis S. H. et al., *Prog. Nucleic Acid Res. & Molecular bio.*, vol. 65, pp. 1-52, 2001).

The PDE-5 activity of each experimental group was shown in Table 3 and FIG. 1.

TABLE 3

| | PDE5A activity (%) | | | | |
|---|---|---|---|---|---|
| no. | 1 μg/ml | 3 μg/ml | 10 μg/ml | 30 μg/ml | 100 μg/ml |
| 1 | 72.15 | 74.94 | 69.11 | 39.97 | 53.23 |
| 2 | 68.41 | 70.61 | 65.10 | 53.93 | 40.14 |
| 3 | 78.80 | 75.10 | 61.95 | 47.99 | 34.21 |
| 4 | 78.02 | 59.02 | 57.00 | 52.30 | 35.31 |
| 5 | 71.05 | 60.06 | 56.10 | 42.51 | 26.64 |
| 6 | 83.18 | 61.50 | 66.89 | 54.09 | 47.78 |
| Average ± SEM | 75.77 ± 2.21 | 66.87 ± 3.08 | 62.67 ± 2.17 | 48.46 ± 2.48 | 39.55 ± 3.95 |

As shown in Table 3, it was found that the PDE-5 activity gradually decreased as the concentration of the EPS according to the present invention increased from 1 μg/mL to 100 μg/mL. This indicates that the EPS according to the present invention inhibits the PDE-5 activity in a concentration-dependent manner. In addition, the $IC_{50}$ value, at which the enzyme activity is reduced by 50%, was 29.5±1.236 μg/mL. Accordingly, these results indicate that the EPS according to the present invention shows sexual function-improving effect even in a small amount.

The invention claimed is:

1. A method for improving sexual function comprising administering to a subject in need of improving sexual function an effective amount of an extracellular polysaccharide produced by *Ceriporia lacerata*; a mycelial culture medium of *Ceriporia lacerata* containing the extracellular polysaccharide; dried powders of the mycelial culture medium of *Ceriporia lacerata* containing the extracellular polysaccharide; or an extract of the mycelial culture medium of *Ceriporia lacerata* containing the extracellular polysaccharide.

2. The method of claim 1, wherein the extracellular polysaccharide comprises 40 to 60 wt % of sugar and 30 to 40 wt % of protein, and has a molecular weight of 100 to 150 kDa.

3. The method of claim 2, wherein the extracellular polysaccharide comprises 43 to 47 wt % of sugar and 33 to 36 wt % of protein, and has a molecular weight of 115 to 125 kDa.

4. The method of claim 2, wherein the sugar contains mannose, galactose and glucose.

5. The method of claim 1, wherein the extracellular polysaccharide is produced a method comprising the steps of:

(a) culturing mycelia of *Ceriporia lacerata* in a liquid to prepare a mycelial culture medium of *Ceriporia lacerata*, (b) drying the mycelial culture medium of *Ceriporia lacerata* to form powders, and (c) extracting the powders of the mycelial culture medium of *Ceriporia lacerata* with a solvent, and filtering and concentrating the resultant extract under reduced pressure.

6. The method of claim 5, wherein the liquid comprises sugar, glucose, starch, sorghum powder, barley powder, soybean flour, magnesium sulfate ($MgSO_4$), monopotassium phosphate ($KH_2PO_4$), dipotassium phosphate ($K_2HPO_4$) and water, and the hydrogen ion concentration of the medium is pH 4.5 to 6.0.

7. The method of claim 5, wherein the culturing of step (a) is conducted under a blue LED light source with a carbon dioxide concentration maintained at 1,000 to 2,000 ppm.

8. The method of claim 1, wherein at least one of the extracellular polysaccharide produced by *Ceriporia lacerata*, the mycelial culture medium of *Ceriporia lacerata* containing the extracellular polysaccharide, the dried powders of the mycelial culture medium of *Ceriporia lacerata* containing the extracellular polysaccharide, and the extract of the mycelial culture medium of *Ceriporia lacerata* containing the extracellular polysaccharide is administered as a pharmaceutical or food composition, said pharmaceutical or food composition comprising the at least one of the extracellular polysaccharide produced by *Ceriporia lacerata*, the mycelial culture medium of *Ceriporia lacerata* containing the extracellular polysaccharide, the dried powders of the mycelial culture medium of *Ceriporia lacerata* containing the extracellular polysaccharide, and the extract of the mycelial culture medium of *Ceriporia lacerata* containing the extracellular polysaccharide in an amount of 0.1 to 80 wt %, as extracellular polysaccharide, based on the total weight of the composition.

9. The method of claim 1, wherein the improving sexual function comprises improving erectile dysfunction or diabetic erectile dysfunction.

10. The method of claim 8, wherein the pharmaceutical composition is in a formulation form selected from the group consisting of tablets, pills, powders, granules, sugar-coated tablets, hard or soft capsules, solutions, suspensions or emulsions, injections, and suppositories.

11. The method of claim 8, wherein the food composition is in a formulation form selected from the group consisting of powders, granules, a tablet, a capsule, a drink, a candy, a chocolate, a gum, a tea, a vitamin complex, and a health supplementary food.

12. The method of claim 8, wherein the composition is administered in an amount of 5 to 500 mg of extracellular polysaccharide per kg of body weight of the subject.

* * * * *